United States Patent
Hubelbank (12)

(10) Patent No.: US 11,672,591 B2
(45) Date of Patent: *Jun. 13, 2023

(54) ILLUMINATED AND ISOLATED ELECTROSURGICAL APPARATUS

(71) Applicant: Medtronic Advanced Energy, LLC, Minneapolis, MN (US)

(72) Inventor: David Hubelbank, Portsmith, NH (US)

(73) Assignee: Medtronic Advanced Energy LLC, Minneapolis, MN (US)

(*) Notice: Subject to any disclaimer, the term of this patent is extended or adjusted under 35 U.S.C. 154(b) by 338 days.

This patent is subject to a terminal disclaimer.

(21) Appl. No.: 17/028,192

(22) Filed: Sep. 22, 2020

(65) Prior Publication Data

US 2021/0007792 A1 Jan. 14, 2021

Related U.S. Application Data

(60) Division of application No. 16/232,705, filed on Dec. 26, 2018, now Pat. No. 10,806,504, which is a
(Continued)

(51) Int. Cl.
*A61B 18/14* (2006.01)
*A61B 90/30* (2016.01)
(Continued)

(52) U.S. Cl.
CPC .......... *A61B 18/1402* (2013.01); *A61B 18/14* (2013.01); *A61B 90/30* (2016.02);
(Continued)

(58) Field of Classification Search
CPC ...... A61B 18/1402; A61B 2018/00083; A61B 2018/00595; A61B 2018/00601; A61B 90/30; A61B 2090/306; A61B 18/14
See application file for complete search history.

(56) References Cited

U.S. PATENT DOCUMENTS 2,888,928 A   6/1959 Seiger
3,677,262 A   7/1972 Henry
(Continued)

FOREIGN PATENT DOCUMENTS

CN   104161584 B   8/2017
CN   1073 74720 A   11/2017
(Continued)

OTHER PUBLICATIONS

U.S. Appl. No. 15/863,049, filed Jan. 5, 2018, First named inventor: Roger Greeley.
(Continued)

*Primary Examiner* — Julianna N Harvey
(74) *Attorney, Agent, or Firm* — Patterson Thuente, P.A.

(57) ABSTRACT

Unintended current flow or plasma discharge has been observed in known illuminated electrosurgical devices having a metallic tubular heat sink surrounding a conductive electrode and an illumination element, and having a distal outer edge that abuts against the light emitting element. An insulating, shielding or other isolating element that prevents or discourages unintended plasma formation between the distal outer edge and nearby patient tissue can reduce the potential for tissue damage to a patient or injury to a surgeon.

23 Claims, 5 Drawing Sheets

Related U.S. Application Data continuation of application No. 15/887,503, filed on Feb. 2, 2018, now Pat. No. 10,194,975.

(60) Provisional application No. 62/531,188, filed on Jul. 11, 2017.

(51) Int. Cl.

| | | |
|---|---|---|
| *F21V 29/503* | (2015.01) | |
| *F21V 29/70* | (2015.01) | |
| *A61B 90/35* | (2016.01) | |
| *F21V 8/00* | (2006.01) | |
| *A61B 18/00* | (2006.01) | |
| *A61B 90/00* | (2016.01) | |
| *F21Y 115/10* | (2016.01) | |
| *F21W 131/20* | (2006.01) | |

(52) U.S. Cl.
CPC ............ *A61B 90/35* (2016.02); *F21V 29/503* (2015.01); *F21V 29/70* (2015.01); *G02B 6/0001* (2013.01); *A61B 2018/00005* (2013.01); *A61B 2018/00083* (2013.01); *A61B 2018/0091* (2013.01); *A61B 2018/00101* (2013.01); *A61B 2018/00595* (2013.01); *A61B 2018/00601* (2013.01); *A61B 2018/1412* (2013.01); *A61B 2090/0427* (2016.02); *A61B 2090/0436* (2016.02); *A61B 2090/306* (2016.02); *F21W 2131/20* (2013.01); *F21Y 2115/10* (2016.08)

(56) References Cited

U.S. PATENT DOCUMENTS

| | | |
|---|---|---|
| 4,207,897 A | 6/1980 | Lloyd et al. |
| 4,244,371 A | 1/1981 | Farin |
| 4,248,224 A | 2/1981 | Mitchiner |
| 4,275,734 A | 6/1981 | van Gerven |
| 4,276,874 A | 7/1981 | Wolvek et al. |
| 4,321,931 A | 3/1982 | Hon |
| 4,342,218 A | 8/1982 | Fox |
| 4,377,168 A | 3/1983 | Rzasa et al. |
| 4,519,389 A | 5/1985 | Gudkin et al. |
| 4,562,838 A | 1/1986 | Walker |
| 4,597,030 A | 6/1986 | Brody et al. |
| 4,598,698 A | 7/1986 | Siegmund |
| 4,601,290 A | 7/1986 | Effron et al. |
| 4,664,110 A | 5/1987 | Schanzlin |
| 4,688,569 A | 8/1987 | Rabinowitz |
| 4,736,749 A | 4/1988 | Lundback |
| 4,779,611 A | 10/1988 | Grooters et al. |
| 4,802,475 A | 2/1989 | Weshahy et al. |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,931,047 A | 6/1990 | Broadwin et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Freidman et al. |
| 5,178,133 A | 1/1993 | Pena |
| 5,207,674 A | 5/1993 | Hamilton |
| 5,217,860 A | 6/1993 | Fahy et al. |
| 5,221,279 A | 6/1993 | Cook et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,250,047 A | 10/1993 | Rydell |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowle |
| 5,334,181 A | 8/1994 | Rubinsky et al. |
| 5,334,193 A | 8/1994 | Nardella et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,443,463 A | 8/1995 | Stern et al. |
| 5,542,196 A | 8/1996 | Hirsch et al. |
| 5,573,424 A | 11/1996 | Poppe |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,817,091 A | 10/1998 | Nardella et al. |

(56) References Cited

U.S. PATENT DOCUMENTS

| | | |
|---|---|---|
| 5,871,523 A | 2/1999 | Fleischman et al. |
| 5,871,525 A | 2/1999 | Edwards et al. |
| 5,873,845 A | 2/1999 | Cline et al. |
| 5,876,399 A | 3/1999 | Chia et al. |
| 5,879,295 A | 3/1999 | Li et al. |
| 5,879,296 A | 3/1999 | Ockuly et al. |
| 5,881,732 A | 3/1999 | Sung et al. |
| 5,882,346 A | 3/1999 | Pomeranz et al. |
| 5,885,278 A | 3/1999 | Fleischman |
| 5,893,848 A | 4/1999 | Negus et al. |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 6,042,556 A | 3/2000 | Beach et al. |
| 6,063,081 A | 5/2000 | Mulier |
| 6,071,279 A | 6/2000 | Whayne et al. |
| 6,088,894 A | 7/2000 | Oakley |
| 6,096,037 A | 8/2000 | Mulier |
| 6,113,592 A | 9/2000 | Taylor |
| 6,117,101 A | 9/2000 | Diederich et al. |
| 6,120,496 A | 9/2000 | Whayne et al. |
| 6,142,994 A | 11/2000 | Swanson et al. |
| 6,293,943 B1 | 9/2001 | Panescu et al. |
| 6,302,880 B1 | 10/2001 | Schaer |
| 6,312,383 B1 | 11/2001 | Lizzi et al. |
| 6,314,962 B1 | 11/2001 | Vaska et al. |
| 6,325,797 B1 | 12/2001 | Stewart et al. |
| 6,364,876 B1 | 4/2002 | Erb et al. |
| 6,385,472 B1 | 5/2002 | Hall et al. |
| 6,398,792 B1 | 6/2002 | O'Connor |
| 6,409,722 B1 | 6/2002 | Hoey |
| 6,419,648 B1 | 7/2002 | Vitek et al. |
| 6,464,700 B1 | 10/2002 | Koblish et al. |
| 6,471,698 B1 | 10/2002 | Edwards et al. |
| 6,488,678 B2 | 12/2002 | Sherman |
| 6,504,985 B2 | 1/2003 | Parker et al. |
| 6,528,954 B1 | 3/2003 | Lys et al. |
| 6,550,926 B2 | 4/2003 | Berger |
| 6,610,057 B1 | 8/2003 | Ellman et al. |
| 6,702,810 B2 | 3/2004 | McClurken |
| 6,786,906 B1 | 9/2004 | Cobb |
| 6,949,098 B2 | 7/2005 | Mulier |
| 7,083,601 B1 | 8/2006 | Cosmescu |
| 7,115,139 B2 | 10/2006 | McClurken |
| 7,942,872 B2 | 5/2011 | Ein-Gal |
| 8,105,323 B2 | 1/2012 | Buysse et al. |
| 8,287,534 B2 | 10/2012 | Dethier et al. |
| 8,506,565 B2 | 8/2013 | DeCarlo |
| 8,690,872 B2 | 4/2014 | Jayaraj |
| 8,882,756 B2 | 11/2014 | Greeley et al. |
| 8,882,767 B2 | 11/2014 | Greep et al. |
| 8,882,768 B2 | 11/2014 | Greep et al. |
| 9,237,922 B2 | 1/2016 | Bromley |
| 9,259,260 B2 | 2/2016 | Greep et al. |
| 9,289,261 B2 | 3/2016 | Shvetsov et al. |
| 9,375,253 B2 | 6/2016 | Greep et al. |
| 9,375,282 B2 | 6/2016 | Nau, Jr. |
| D761,962 S | 7/2016 | Fleenor |
| 9,851,060 B2 | 12/2017 | Vinod |
| 10,194,975 B1 * | 2/2019 | Hubelbank ............ F21V 29/503 |
| 10,806,504 B2 * | 10/2020 | Hubelbank ........ A61B 18/1402 |
| 2002/0049483 A1 | 4/2002 | Knowlton |
| 2002/0058938 A1 | 5/2002 | Cosmescu et al. |
| 2002/0062131 A1 | 5/2002 | Gallo, Sr. |
| 2002/0107517 A1 | 8/2002 | Witt et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0024395 A1 | 2/2004 | Ellman et al. |
| 2004/0030328 A1 | 2/2004 | Eggers et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischel |
| 2004/0162552 A1 | 8/2004 | McClurken |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0090816 A1 | 4/2005 | McClurken |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |
| 2006/0041254 A1 | 2/2006 | Francischelli et al. |
| 2006/0064085 A1 | 3/2006 | Schechter et al. |
| 2006/0116675 A1 | 6/2006 | McClurken |
| 2006/0149225 A1 | 7/2006 | McClurken |
| 2007/0043397 A1 | 2/2007 | Ocel et al. |
| 2007/0049920 A1 | 3/2007 | Greeley et al. |
| 2007/0049927 A1 | 3/2007 | Saltzman |
| 2007/0093808 A1 | 4/2007 | Mulier et al. |
| 2007/0118114 A1 | 5/2007 | Miller et al. |
| 2007/0208226 A1 | 9/2007 | Grey et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0058587 A1 | 3/2008 | O'Brien et al. |
| 2008/0071270 A1 | 3/2008 | Desinger et al. |
| 2008/0207208 A1 | 8/2008 | Schutz |
| 2009/0054890 A1 | 2/2009 | Decarlo |
| 2009/0264879 A1 | 10/2009 | Greeley et al. |
| 2009/0306655 A1 | 12/2009 | Stangenes |
| 2010/0100095 A1 | 4/2010 | Greeley et al. |
| 2010/0145333 A1 | 6/2010 | Dethier |
| 2011/0060332 A1 | 3/2011 | Cheng |
| 2011/0118735 A1 * | 5/2011 | Abou-Marie ...... A61B 18/1492 606/45 |
| 2011/0178515 A1 | 7/2011 | Bloom et al. |
| 2011/0190768 A1 | 8/2011 | Shvetsov |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0101496 A1 | 4/2012 | McClurken et al. |
| 2012/0116397 A1 | 5/2012 | Rencher et al. |
| 2012/0151165 A1 | 6/2012 | Conley et al. |
| 2012/0191084 A1 | 7/2012 | Davison et al. |
| 2012/0253343 A1 | 10/2012 | McClurken et al. |
| 2012/0265184 A1 | 10/2012 | Sliwa et al. |
| 2012/0283718 A1 | 11/2012 | Cosmescu |

(56) References Cited

U.S. PATENT DOCUMENTS

| | | |
|---|---|---|
| 2012/0283728 A1 | 11/2012 | Cosmescu |
| 2013/0267786 A1 | 10/2013 | Vayser et al. |
| 2014/0221763 A1 | 8/2014 | Vayser et al. |
| 2014/0276763 A1 | 9/2014 | Greep et al. |
| 2016/0045247 A1 | 2/2016 | Heim et al. |
| 2016/0157920 A1* | 6/2016 | Vayser .................. A61B 90/30 600/249 |
| 2016/0278874 A1 | 9/2016 | Fleenor |
| 2017/0071667 A1* | 3/2017 | Leung .................. A61B 90/39 |
| 2018/0078301 A1 | 3/2018 | Vayser |

FOREIGN PATENT DOCUMENTS

| | | |
|---|---|---|
| CN | 304557543 S | 3/2018 |
| WO | WO 9510981 A1 | 4/1995 |
| WO | WO 2011127902 A1 | 10/2011 |
| WO | WO 2012118746 A2 | 9/2012 |
| WO | WO 2014/036118 A1 | 3/2014 |
| WO | WO 2014165551 A1 | 10/2014 |
| WO | WO 2015085108 A1 | 6/2015 |
| WO | WO 2016196562 A1 | 12/2016 |
| WO | WO 2018/080963 A1 | 5/2018 |

OTHER PUBLICATIONS

U.S. Appl. No. 62/543,497, filed Aug. 10, 2017, First named inventor: David Hubelbank.

U.S. Appl. No. 62/395,529, filed Sep. 16, 2016. Inventor: Alex Vayser. Title: "Methods and Apparatus for Electrosurgical Illumination", Applicant: Invuity, Inc.

Letter from Department of Health & Human Services to Invuity, Inc., pp. 1-7 (Sep. 15, 2016).

Bennett, et al., "Assessment of Penetrating Thermal Tissue Damage/Spread Associated with PhotonBlade,Valleylab Pencil, Valleylab, EDGE, Coated Pencil, PlasmaBlade 3.0S and PlasmaBlade 4.0 for Intraoperative Tissue Dissection using the Fresh Extirpated Porcine Muscle Model" (2017), https://www.spiedigitallibrary.org/conferenceproceedings-of-spie/10066/1/Assessment-of-penetrating-thermal-tissue-damage-spread-associate-with-PhotonBlade/10.1117/12.2252111.short?SSO=1.

Class 2 Device Recall INVUITY PHOTON BLADE, Jun. 12, 2017, 1 page, https://www.accessdata.fda.gov/scripts/cdrh/cfdocs/cfRes/res.cfm/ID=156761.

IEC 60601-2-2 CORR 1—Medical Electrical Equipment—Part 2-2: Additional information in instructions for use Fifth Edition, 1 page (2009).

IEC 60601-2-2—Medical Electrical Equipment—Part 2-2: Particular requirements for the basic safety and essential performance of high frequency surgical equipment and high frequency surgical accessories—Edition 6.0, 190 pp (Mar. 2017).

Invuity Press Release, Sep. 25, 2017, "Invuity Announces Full Commercial Launch of Photonblade", 1 page, http://investors.invuity.com/phoenix.zhtml?c=253978&p=irol-NewsArticle_print&ID=2302681.

Invuity Press Release, Jun. 13, 2017, "Invuity Provides Update on Photonblade Commercialization", pp. 1-2.

Invuity Press Release, Jul. 25, 2017, "Invuity Reports 2017 Second Quarter, Six-Month Financial Results", pp. 1-2.

Product Brochure, Invuity PhotonBlade, downloaded from ttp://invuity.com/products/photonblade on Jun. 19, 2017.

MAUDE Adverse Event Report; INVUITY, INC. PHOTONBLADE, FDA, https://www.accessdata.fda.gov/scripts/cdrh/cfdocs/cfmaude/detail.cfm?mdrfoi_id=6679528&pc=GEI, Event Date: Jun. 9, 2017.

MAUDE Adverse Event Report; INVUITY, INC. PHOTONBLADE, FDA, https://www.accessdata.fda.gov/scripts/cdrh/cfdocs/cfmaude/detail.cfm?mdrfoi_id=6679521&pc=GEI, Event Date: June 5, 2017.

MAUDE Adverse Event Report; INVUITY, INC. PHOTONBLADE, FDA, https://www.accessdata.fda.gov/scripts/cdrh/cfdocs/cfmaude/detail.cfm?mdrfoi_id=6679511&pc=GEI, Event Date: June 2, 2017.

MAUDE Adverse Event Report; INVUITY, INC. PHOTONBLADE, FDA, https://www.accessdata.fda.gov/scripts/cdrh/cfdocs/cfmaude/detail.cfm?mdrfoi_id=6679508&pc=GEI 2, Event Date: May 23, 2017.

US Securities and Exchange Commission, EDGAR database, Form 10Q, Signed Jul. 26, 2017, https://www.sec.gov/Archives/edgar/data/1393020/000155837017005346/ivty-20170630x10q.htm.

US Securities and Exchange Commission, EDGAR database, Form 10Q, Signed Nov. 7, 2017, https://www.sec.gov/Archives/edgar/data/1393020/000155837017008398/ivty-20170930x10q.htm.

* cited by examiner

ILLUMINATED AND ISOLATED ELECTROSURGICAL APPARATUS

CROSS-REFERENCE TO RELATED APPLICATIONS

This application is a divisional of U.S. application Ser. No. 16/232,705, filed Dec. 26, 2018 (now U.S. Pat. No. 10,806,504 B2), which is a continuation of U.S. application Ser. No. 15/887,503, filed Feb. 2, 2018 (now U.S. Pat. No. 10,194,975 B1), which claims priority to U.S. Provisional Application No. 62/531,188 filed Jul. 11, 2017, the entire disclosures of which are incorporated herein by reference.

TECHNICAL FIELD

The present application relates to illuminated electrosurgical devices.

BACKGROUND

Illuminated electrosurgical devices generally include a hand piece (handle) ergonomically adapted for ease of manipulation by a surgeon during surgery, and for positioning an energy tip of the device to deliver electrical energy to a target tissue for tissue cutting or coagulation. An electrode and electrical supply cable are generally disposed within the handle, traversing from the handle's proximal end through the handle body, and terminating in an energy discharge tip at the distal end of the device. The electrical supply cable typically is connected to an energy source, such as a radiofrequency (RF) energy generator.

The handle or other portion of the device may include an illumination element for illuminating the surgical field. Light may be conducted towards the energy discharge tip and directed onto the surgical field via an optical waveguide coupled to the handle or disposed within the handle. The electrode may be disposed within the optical waveguide, or disposed alongside the waveguide. The electrode and waveguide may be disposed within a suitable supporting structure (for example, a cylindrical metal tube), that may be slidably extendable or retractable to permit the electrosurgical device to elongate or shorten as needed to treat the surgical site.

SUMMARY

The present invention provides an improved illuminated electrosurgical device having reduced tendency to cause unintended current flow or plasma discharge and patient injury. In one embodiment, the device comprises:
 a) a handle;
 b) a conductive electrode supported by the handle and having a tip for cutting or cauterizing tissue;
 c) an illumination element coupled to the handle, the illumination element comprising a light source, an optical waveguide, and a light emitting element illuminating the electrode tip;
 d) a metallic tubular heat sink surrounding at least part of the conductive electrode and illumination element and having a distal outer edge that abuts against the light emitting element; and
 e) an insulating, shielding or other isolating element that prevents or discourages unintended current flow or plasma formation between the distal outer edge and nearby patient tissue.

The disclosed invention addresses shortcomings in current electrosurgical devices, by preventing or discouraging unintended RF energy release and accidental injury to the patient or surgeon. The invention includes modification of a known device to insulate, isolate or shield the distal end of a metal heat sink on such device (for example, by adding electrical insulation over the distal end), thereby preventing or discouraging the unwanted release of energy.

The above summary is not intended to describe each illustrated embodiment or every implementation of the disclosed subject matter. The details of one or more embodiments of the invention are set forth in the accompanying Drawing and this Specification. Other features, objects, and advantages of the invention will be apparent from the Drawing, the Specification and the claims.

BRIEF DESCRIPTION OF THE DRAWING

The disclosed subject matter may be more completely understood from the accompanying figures, in which.

Like reference symbols in the various figures of the Drawing indicate like elements. The elements in the Drawing are not to scale.

DEFINITIONS

Unless the context indicates otherwise, the following terms shall have the following meaning and shall be applicable both to the singular and plural:

The terms "conductor", "conductive" and "conducting" mean electrically conductive, and refer to materials that readily permit the flow of electrical current through such material. Conductive materials may in some instances be thermally conductive but are not always so. Materials such as carbon black, moisture and metals are representative conducting materials.

The term "electrosurgical device" means an electrical device designed for handheld use by a surgeon to dispense RF or other energy through the tip of an electrode into target surgical tissue, in order to cut or coagulate the tissue during a surgical procedure.

The terms "insulator", "insulation" and "insulating" mean electrically insulating, and refer to dielectric materials that permit little, if any, flow of electrical current through such material. Insulating materials may in some instances be thermal insulators but are not always so. Materials such as glass, metal oxides, porcelain, paper, plastics, polymers and rubbers are representative insulating materials.

The terms "radiofrequency energy" or "RF" energy mean energy from the electromagnetic spectrum having a frequency between about 3 kilohertz (3 kHz) and about 300 gigahertz (300 GHz).

DETAILED DESCRIPTION

Surgical devices should not unduly impede the surgeon's view of the operating field. This is particularly troublesome in electrosurgical devices, especially those with extra features beyond energy delivery, such as added illumination, smoke evacuation, saline delivery, or other ancillary features.

In the case of an electrosurgical device which also provides added illumination (viz. light directed at the surgical field), the light desirably is emitted near the distal end of the device, where any added bulk may also directly impede the surgeon's view. Device designers have consequently sought to minimize the distal profile of such devices, and to make the associated components as small, thin and few in number as possible.

Figure 1:
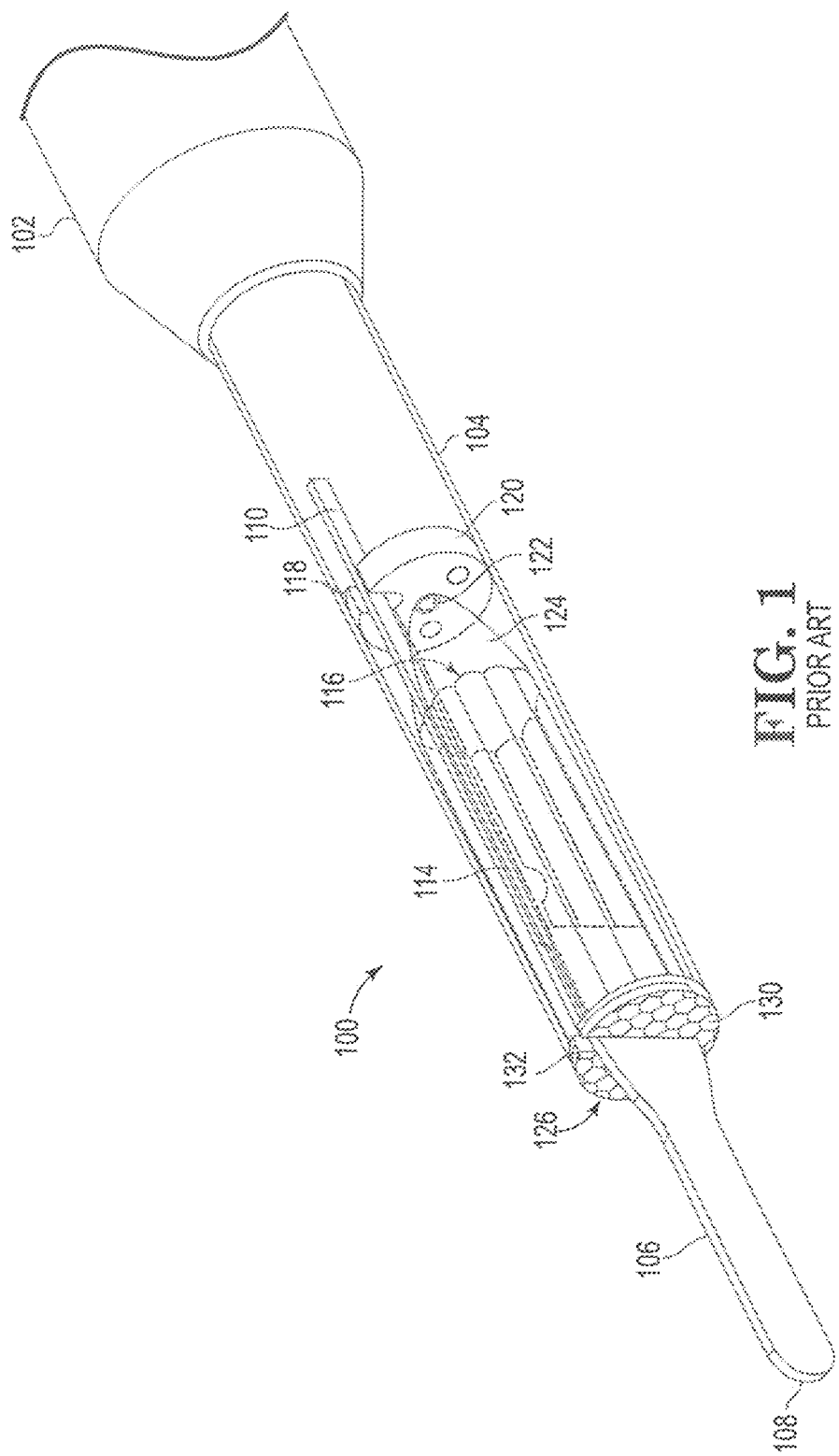
FIG. 1 is a perspective view, partially in section, of a known illuminated electrosurgical device.

FIG. 1 shows a known electrosurgical device 100 supplied by Invuity, Inc. as the PhotonBlade™ electrosurgical device. Device 100 includes a handle 102 in which is mounted a tubular metal heat sink 104 that can be slidably extended from or pushed into handle 102 and fixed in place with a collet or other locking mechanism (not shown in FIG. 1). Doing so permits a surgeon to vary the length of device 100 as may be needed for particular surgical procedures. Conductive electrode 106 is partially housed within heat sink 104, and includes a distally projecting RF energy discharge tip 108 intended to emit RF energy to cut or cauterize human or animal tissue. Electrode 106 also includes a conductive leg portion 110 extending towards handle 102, and intended to be connected (e.g., via an electrical connector, solder or other suitable connection not shown in FIG. 1) with a conductive cable (also not shown in FIG. 1) that passes through handle 102 and supplies RF energy to electrode 106. Optionally, the electrode 106 may include an enamel insulative coating such as those disclosed in U.S. Pat. No. 7,736,361 B2. Leg portion 110 resides in a slot 112 formed in optical waveguide 116 and passes through a notch 118 in light source 120, shown here as a circuit board housing a light emitting diode (LED) 122. Light from LED 122 is captured by parabolic light collector 124 and transmitted through waveguide 116 towards translucent light emitting element 126. A layer of cladding 128 surrounds optical waveguide 116 and is said to provide desired optical properties to optical waveguide 116. The front or distal end of heat sink 104 abuts against the rear or proximal face of light emitting element 126. During use of device 100, light is emitted from lenslets 130 on the front face of element 126, as well as from outer edge 132 of element 126.

Figure 2:
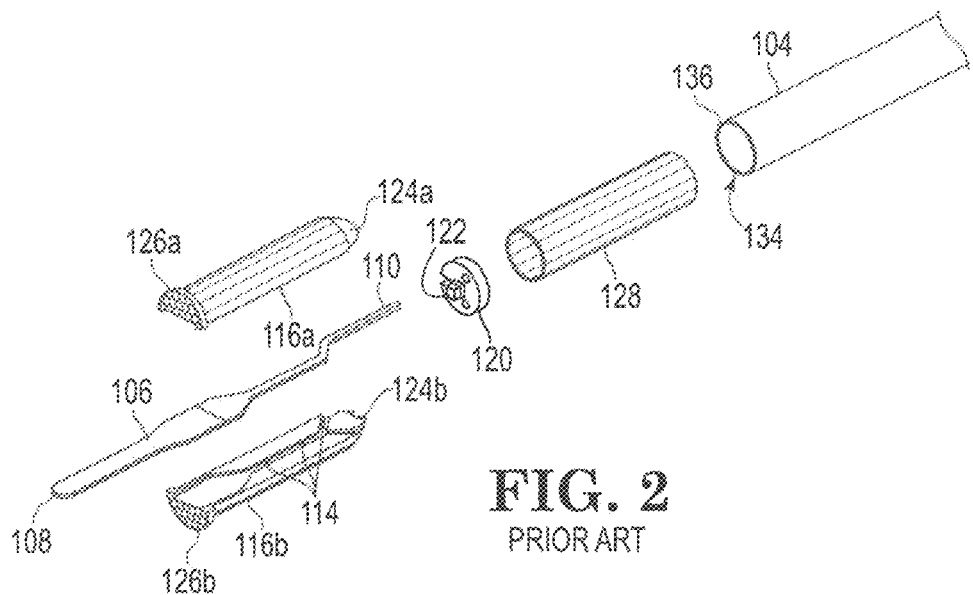
FIG. 2 is an exploded view of distal components of the FIG. 1 device.

FIG. 2 shows an exploded view of distal components of the FIG. 1 device. Optical waveguide 116, collector 124 and light emitting element 126 are respectively formed from half guides 116a and 116b, half collectors 124a and 124b, and half elements 126a and 126b. Slot 114 and cladding 122 have the shapes shown in FIG. 2. As supplied in device 100, tubular metal heat sink 104 has a thin outer layer of insulation (not labeled in FIG. 2). Cut end 134 of heat sink 104 is however not insulated, and cut end 134, and especially its outer edge 136, have a high electrical potential and can promote unintended RF discharge.

Figure 3:
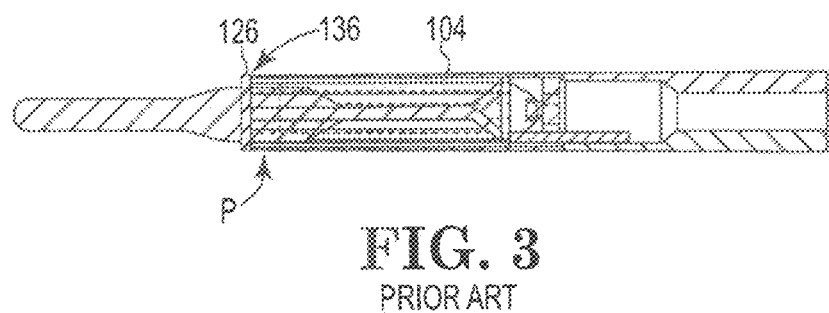
FIG. 3 is a cross-sectional view of the assembled FIG. 2 components.

FIG. 3 is a cross-sectional view of the assembled FIG. 2 components. Cut end 134 abuts against the rear face of light emitting element 126. Arrow P indicates a point from which unintended RF energy may be emitted from device 100 toward tissue beneath device 100, especially when high power levels (e.g., power levels of at least 10 watts, at least 20 watts, at least 30 watts, at least 40 watts or at least 50 watts) are employed. When such emission occurs, current can flow or plasma can form between cut end 134 or outer edge 136 and nearby tissue, causing tissue burning at other than the intended surgical site, while meanwhile depowering electrode 106 and preventing tip 108 from cutting or cauterizing target tissue.

Figure 11:
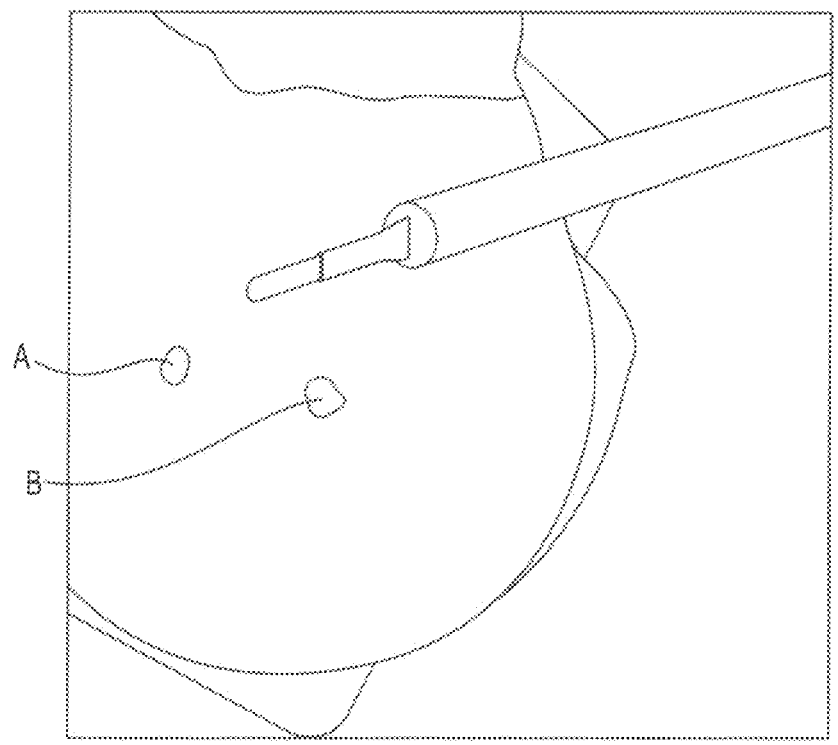
FIG. 11 is a photograph showing the unintended discharge of energy from the FIG. 1 device onto nearby tissue.

FIG. 11 is a photograph showing such unintended current flow or plasma formation, in a simulated electrosurgery performed as described in Example 1. Burn marks A and B were caused by two prior unintended plasma bursts, and an unintended plasma formed under the distal end of heat sink 104.

Figure 4:
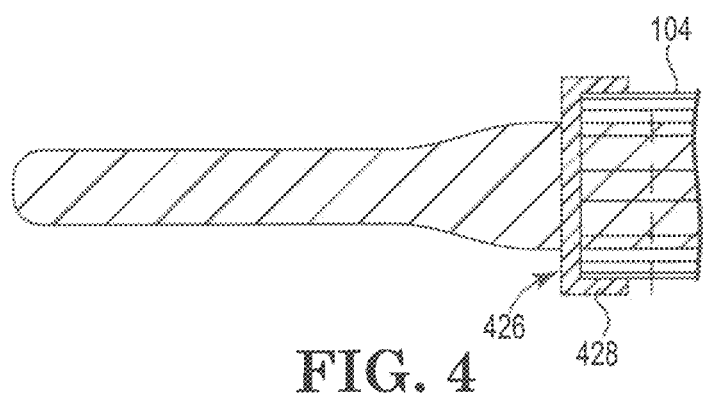
FIG. 4 through FIG. 10 are sectional views of various embodiments of the invention.

FIG. 4 shows one solution to the unintended current flow or plasma generation problem discussed above. Light emitting element 426 has a larger outside diameter than heat sink 104, and includes a rim portion 428 that extends proximally along at least a portion of heat sink 104 (e.g., at least 1 mm, at least 2 mm, at least 3 mm, at least 4 mm or at least 5 mm, and up to 10 mm, up to 9 mm or up to 8 mm) and has sufficient thickness (e.g., at least 0.2 mm, at least 0.3 mm, at least 0.4 mm or at least 0.5 mm, and up to 2 mm, up to 1.8 mm, up to 1.6 mm or up to 1.5 mm) so that cut end 134 and edge 136 are buried within and insulated by rim portion 428. This improves the electrical isolation of cut end 134, and discourages or prevents unintended current flow or plasma generation. The thickness and length of rim portion 428 (and the thickness, shape or composition of the other insulating, shielding or other isolating measures discussed below) may be empirically determined, for example by repeating the chicken tissue test discussed above and in Example 1, or by measuring breakdown voltage using the Hi-Pot test discussed in Example 2. In certain embodiments, the added insulating, shielding or other isolating measure is sufficient to prevent unintended current flow or plasma generation when using the Example 1 experimental setup and an operating power of 10 watts, 20 watts, 30 watts, 40 watts or 50 watts, while contacting the chicken tissue with the light emitting element, or while laying the heat sink atop the tissue. In certain other embodiments, the added insulating, shielding or other isolating measure is sufficient to increase the breakdown voltage using the Example 2 Hi-Pot test and the metal heat sink alone without the handle and tip, to at least 2 KV RMS @20 seconds, at least 3 KV RMS @20 seconds or at least 4 KV RMS @20 seconds.

Figure 5:
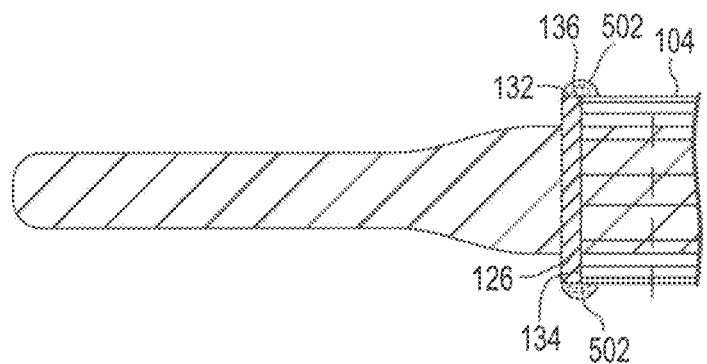

FIG. 5 shows another solution to the unintended current flow or plasma generation problem discussed above. A bead 502 of a suitable curable or hardenable insulating material (e.g., a room temperature vulcanizing silicone resin, a curable thermoset epoxy or other preferably thermosetting insulating material, a hardenable inorganic liquid such as waterglass or a hardenable inorganic paste such as plaster of Paris) is placed over outer edge 132 of light emitting element 126 and over outer edge 136 and at least a portion of the distal end of heat sink 104, and then cured or hardened. In an embodiment, a bead of the insulating material is applied to light emitting element 126 before heat sink 104 is abutted against element 126, followed by pushing heat sink 104 and element 126 together, so that cut end 134 will contact and be embedded in bead 502. If a translucent or transparent insulating material is employed for bead 502, or if the width of bead 502 is such that a portion of outer edge 132 of element 126 remains uncovered, then light may continue to be emitted from outer edge 132 during surgery. This may be desirable in some instances, but may be undesirable in others. For example, if an opaque insulating material is employed for bead 502, light may no longer be emitted from outer edge 132, and glare may be reduced or eliminated during surgery. If desired, the axial length of element 126 may be increased so that outer edge 132 may be made wider, thereby permitting bead 502 to be made wider as well while preserving or largely preserving the original width of outer edge 132. In any event, the thickness, width and composition of bead 502 may be empirically determined using the Example 1 or Example 2 procedures discussed above in connection with the FIG. 4 embodiment. Bead 502 may for example have a thickness of at least 0.1 mm, at least 0.2 mm, at least 0.3 mm, at least 0.4 mm or at least 0.5 mm, and up to 2 mm, up to 1.5 mm or up to 1 mm. Bead 502 may for example have a width of at least 1 mm, at least 2 mm, at least 3 mm, at least 4 mm or at least 5 mm, and up to 10 mm, up to 9 mm or up to 8 mm.

Figure 6:
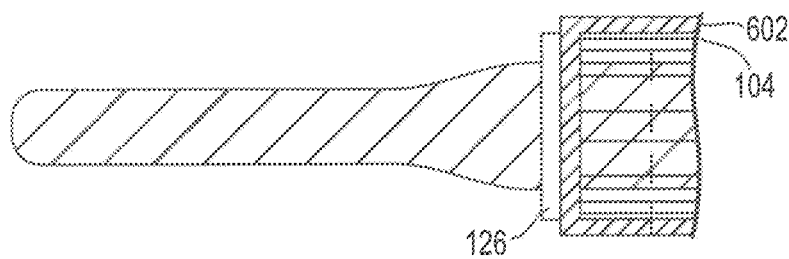

FIG. 6 shows another solution to the unintended current flow or plasma generation problem discussed above. An insulating coating 602 (preferably a coating that is thicker, less conductive, or both thicker and less conductive than the insulative layer currently employed on heat sink 104) is coated onto cut end 134 and over at least a portion of heat sink 104. Coating 602 may for example be a paint, a vapor-deposited polymeric film, a cured or hardened layer of an organic or inorganic material, or a layer of glass. In a preferred embodiment, coating 602 also covers at least a portion of the inner sidewall of heat sink 104, and may for example extend along heat sink 104 past the proximal end of leg 110. The thickness, width, composition and configuration of coating 602 may be empirically determined using the Example 1 or Example 2 procedures discussed above in connection with the FIG. 4 embodiment. Coating 602 may for example have a thickness of at least 0.05 mm, at least 0.1 mm, at least 0.2 mm, at least 0.3 mm, at least 0.4 mm or at least 0.5 mm, and up to 2 mm, up to 1.5 mm or up to 1 mm. Coating 602 may for example extend proximally away from cut edge 134 along the inner or outer sidewalls of heat sink 104 for a distance of at least 1 mm, at least 2 mm, at least 3 mm, at least 4 mm or at least 5 mm, and up to the entire length of heat sink 104, past the proximal end of leg 110, or for at least the distal 20 mm, 10 mm or 8 mm of heat sink 104.

Figure 7:
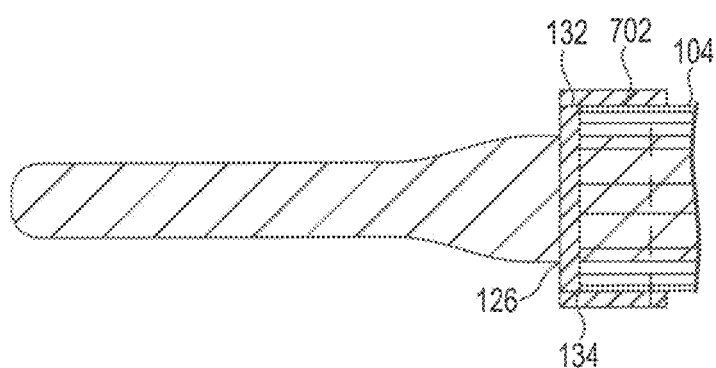

FIG. 7 shows another solution to the unintended current flow or plasma generation problem discussed above. A length of rubber or plastic tubing 702 is placed over cut end 134 and over at least a portion of outer edge 132 of element 126 and over at least a portion of the distal end of heat sink 104, to form an insulating sleeve or collar. Tubing 702 may for example be an elastomeric tubing material such as surgical or other tubing made from natural rubber, fluoroelastomer, latex, silicone or polyvinyl chloride (PVC). Tubing 702 may also be a heat-shrinkable tubing such as a polyolefin, neoprene or fluoropolymer material. The thickness, width and composition of tubing 702 may be empirically determined using the Example 1 or Example 2 procedures discussed above in connection with the FIG. 4 embodiment. Tubing 702 may for example have a thickness of at least 0.1 mm, at least 0.2 mm, at least 0.3 mm, at least 0.4 mm or at least 0.5 mm, and up to 2 mm, up to 1.5 mm or up to 1 mm. Tubing 702 may for example have a width of at least 2 mm, at least 3 mm, at least 4 mm or at least 5 mm, and up to 10 mm, up to 9 mm or up to 8 mm.

Figure 8:
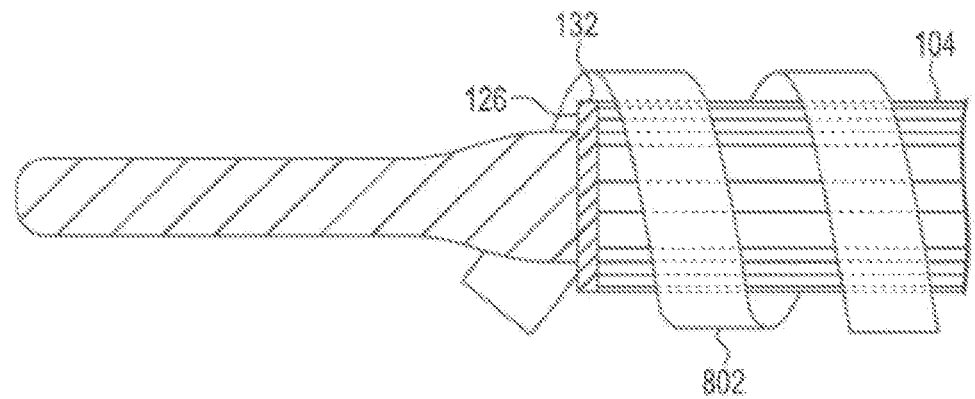

FIG. 8 shows another solution to the unintended current flow or plasma generation problem discussed above. A least one and preferably two or more turns of adhesive tape (e.g., PVC electrical tape) 802 are wrapped around at least a portion of outer edge 132 of element 126, over cut end 134 and over at least a portion of the distal end of heat sink 104. A spiral wrap pattern or a wrap pattern in which the ends of the tape are aligned with and overlap one another may be used. The thickness, width, composition and number of turns of tape 802 may be empirically determined using the Example 1 or Example 2 procedures discussed above in connection with the FIG. 4 embodiment. Tape 802 may for example have a thickness of at least 0.1 mm, at least 0.2 mm or at least 0.3 mm, and up to 2 mm, up to 1.5 mm or up to 1 mm. Tape 702 may for example have a width of at least 2 mm, at least 3 mm, at least 4 mm or at least 5 mm, and up to 20 mm, up to 16 mm or up to 10 mm.

Figure 9:
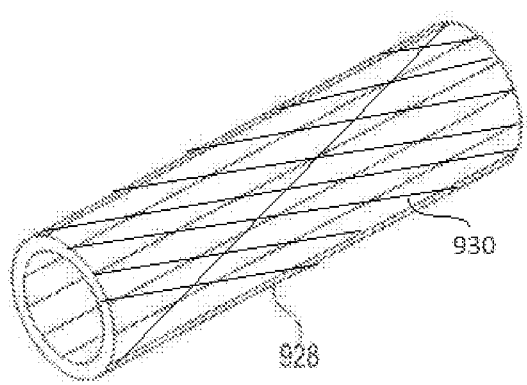

FIG. 9 shows another solution to the unintended current flow or plasma generation problem discussed above. The thickness, composition or both thickness and composition of cladding 928 are changed to increase the breakdown voltage exhibited by heat sink 104. The extent to which such changes are made may be empirically determined using the Example 1 or Example 2 procedures discussed above in connection with the FIG. 4 embodiment. Cladding 928 may for example have a thickness of at least 0.1 mm, at least 0.2 mm or at least 0.3 mm, and up to 2 mm, up to 1.5 mm or up to 1 mm, and may be made from a variety of suitable dielectric materials including ceramics, glass, paper, plastics and rubber.

Figure 10:
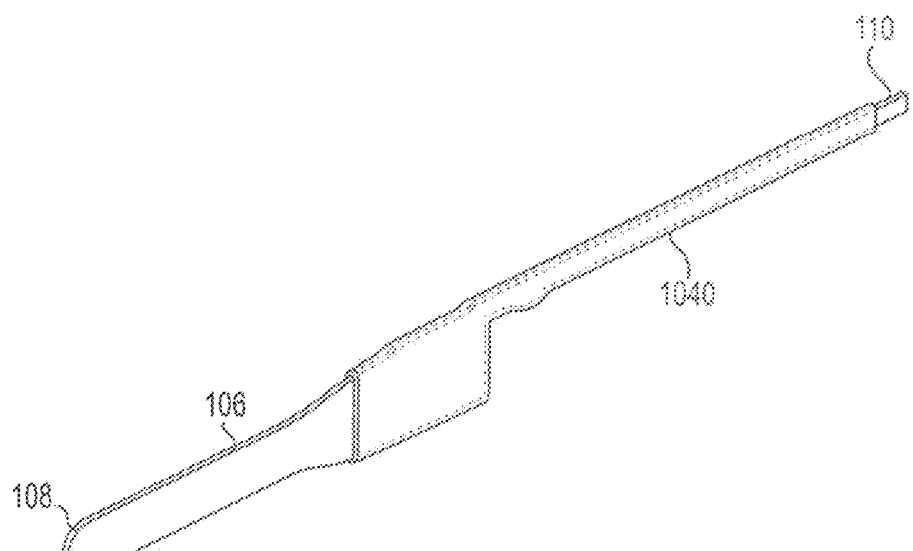

FIG. 10 shows another solution to the unintended current flow or plasma generation problem discussed above. Some or all of the portions of electrode 106 that contact light emitting element 126 or that extend through heat sink 104 (and especially those parts of electrode 106 such as leg 110 which are positioned near the inner wall of heat sink 104) can be coated with a layer 1040 of a suitable insulating material to increase the breakdown voltage exhibited by heat sink 104. The thickness, arrangement and composition of such a coating may be empirically determined using the Example 1 or Example 2 procedures discussed above in connection with the FIG. 4 embodiment. Coating 1040 may for example have a thickness of at least 0.1 mm, at least 0.2 mm or at least 0.3 mm, and up to 2 mm, up to 1.5 mm or up to 1 mm, and may be made from a variety of suitable dielectric materials including ceramics, glass, paper, plastics and rubber.

In an additional embodiment, shown in FIG. 9, a continuous or discontinuous (e.g., screened) conductive layer 930 may be placed between cladding 928 and heat shield 104, and connected to an earth ground. Doing so can reduce the voltage potential at cut end 134 and along the length of heat shield 104, and discourage unintended external current flow or plasma generation. The additional conductive layer 930 may if desired be included as a part of cladding 928 (for example, as an outer layer) or may be included as a part of heat sink 104 (for example, as an inner layer separated from the inner metallic wall of heat sink 104 by a suitable insulating layer on such inner wall. When such an additional conductive layer 930 is employed, it may also be necessary or desirable to employ additional insulating measures on portions of the device inside the additional conductive layer 930 (for example, by making changes to cladding 928 as discussed in connection with FIG. 9, or by coating portions of electrode 106 as discussed in connection with FIG. 10), so as to avoid undesirable internal current leakage or internal current flow or plasma generation during use.

In an additional embodiment, not shown in the Drawing, electrode 106 and one or more of optical waveguide 116, light source 120, light collector 124 and light emitting element 126 can be redesigned so that those portions of electrode 106 that lie inside heat sink 104 are further from the inner wall of heat 110 than is presently the case in device 100. In one embodiment, electrode 106 may be made narrower as it passes through light emitting element 126 and optical waveguide 116. In the same or another embodiment, leg 110 is rerouted so that it runs through the center of device 100 rather than near the inner wall of heat sink 104, and light source 120 and light collector 124 are modified so that LED 122 is not in the way of leg 110 and optical waveguide 116 is edge-lit rather than centrally illuminated.

In an additional embodiment, not shown in the Drawing, all or at least a distal portion of heat sink 104 is made from an insulating material rather than from metal. Exemplary such materials include ceramics, glass and plastics. The thickness, composition and configuration of such an insulating material may be empirically determined using the Example 1 or Example 2 procedures discussed above in connection with the FIG. 4 embodiment.

The various insulation materials mentioned above may be interchanged for one another or replaced or combined with a variety of other insulation materials. Preferred insulation materials include acrylics, acrylates, acrylonitrile-butadiene-styrene (ABS) copolymers, cyanoacrylate adhesives, epoxies, fluorinated ethylene propylene (FEP) elastomers, polycarbonates, polyimides, polytetrafluoroethylene (PTFE) plastics, natural and synthetic rubbers, non-conductive adhesives, RTV and other silicone rubbers, polyurethanes, inorganic dielectrics, glass, ceramics, porcelain, and other insulating materials that will be familiar to persons having ordinary skill in the art.

EXAMPLES

Example 1

Simulated Electrosurgery

Simulated electrosurgery was performed using a skinless chicken breast, a Valleylab Force FX™ isolated output electrosurgical generator set to 50 watt, high coagulation output, and device 100. The device had previously been used in an electrosurgical procedure. The results are shown in FIG. 11. Burn marks A and B were caused by two prior unintended current or plasma bursts when device 100 was held at an angle and light emitting element 126 was allowed to contact the tissue. An unintended plasma was visible under the distal end of heat sink 104. Meanwhile electrode 106 is depowered and energy discharge tip 108 cannot be used for cutting or cauterizing target tissue. The tendency for unintended plasma generation to occur increased significantly whenever device 100 was held at an acute angle with respect to the chicken tissue, and increased as the distance from end 134 to the tissue diminished. At a sufficiently small distance or upon contact of light emitting element 126 against the tissue, an unintended plasma discharge commenced. Unintended plasma generation also occurred whenever heat sink 104 was laid atop the tissue. The plasma continued until device 100 was pulled or tipped away from the tissue, and meanwhile the tissue became charred and the odor of cooked chicken emanated from the burn sites. Upon removal from the tissue, a dark discolored region was visible near the portion of edge 134 that had been closest to the tissue, and the corresponding bluish insulation layer on heat sink 104 appeared to have been burned away.

These results suggest that in tight anatomical spaces where contact between the edge of the metal heat sink tube and tissue cannot be avoided, tissue damage will likely occur due to RF energy release between the distal edge of the metal tube and the surgical target tissue, particularly when the device is used for coagulation.

Example 2

IEC Hi-Pot Test

International Standard IEC 60601-2-2 (the IEC Hi-Pot Test) may be used to test dielectric strength and leakage current for both monopolar and bipolar high frequency electrosurgical devices, and their individual components. An Invuity PhotonBlade electrosurgical device that had previously been used in a surgical procedure was disassembled and its components subjected to the IEC Hi-Pot Test to determine breakdown voltages and evaluate potential energy leakage for various components and subassemblies. The Valleylab Force FX™ electrosurgical generator used in Example 1 was employed for the IEC test. The Force FX generator has a maximum voltage output of 3.89 KV RMS. Each of the handle 102 only (without the heat sink 110 and the components it contains); the handle 102 with the heat sink 110 and the components it contains (but without buttons); the handle 102 and its cable (but without buttons and without heat sink 110 and the components it contains); and the heat sink 110 and some of components it contains (but without handle 102 and the exposed portion of electrode 106) were evaluated for potential energy leakage. The test results are shown below in Table 1.

TABLE 1

| Test Setup | Failure Voltage |
|---|---|
| Handle Only (no Heat Sink) | 3.89 KV RMS @ 20 seconds |
| Handle and Heat Sink (no Buttons) | 2.7 KV RMS @ 20 seconds |
| Handle and Cable (no Buttons and no Heat Sink) | 3.01 KV RMS @ 20 seconds |
| Heat Sink Only (no Handle or Tip) | 1.6 KV RMS @ 20 seconds |

The results in Table 1 show that each of the tested components may have voltage breakdown issues, with the heat sink representing the weakest tested link.

Various embodiments of systems, devices, and methods have been described herein. These embodiments are given only by way of example and are not intended to limit the scope of the claimed invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions. For example, persons of ordinary skill in the relevant art will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

For purposes of interpreting the claims, it is expressly intended that the provisions of 35 U.S.C. § 112(f) are not to be invoked unless the specific terms "means for" or "step for" are recited in a claim.

The invention claimed is:

1. An electrosurgical device comprising:
  a) a handle;
  b) a conductive electrode supported by the handle and having a tip for cutting or cauterizing tissue;
  c) an illumination element coupled to the handle, the illumination element comprising a light source, an optical waveguide, and a light emitting element illuminating the electrode tip;
  d) a metallic tubular heat sink surrounding at least part of the conductive electrode and illumination element and having a distal outer edge that abuts against the light emitting element; and
  e) an insulating, shielding or other isolating element that prevents or discourages unintended current flow or plasma formation between the distal outer edge and nearby patient tissue
  wherein the heat sink has inner and outer sidewalls; the insulating, shielding or other isolating element covers at least a portion of the inner sidewall; the electrode has a proximal end; and the insulating, shielding or other isolating element extends along the inner sidewall past such proximal end.

2. The device of claim 1, wherein the insulating, shielding or other isolating element also surrounds the distal outer edge.

3. The device of claim 1, wherein the insulating, shielding or other isolating element also covers at least a portion of the outer sidewall.

4. The device of claim 1, wherein the insulating, shielding or other isolating element also comprises an insulating coating on the distal outer edge and over at least a portion of the heat sink.

5. The device of claim 1, wherein the insulating, shielding or other isolating element comprises a paint, vapor-deposited polymeric film, cured or hardened layer of an organic or inorganic material, or layer of glass.

6. The device of claim 1, wherein the insulating, shielding or other isolating element also comprises a length of rubber or plastic tubing placed over the distal outer edge, over at least a portion of the light emitting element, and over at least a portion of the distal end of the heat sink, to form an insulating sleeve or collar.

7. The device of claim 6, wherein the tubing comprises an elastomeric natural rubber, fluoroelastomer, latex, silicone or polyvinyl chloride.

8. The device of claim 6, wherein the tubing comprises heat-shrinkable tubing.

9. The device of claim 1, wherein the insulating, shielding or other isolating element also comprises cladding that surrounds the optical waveguide and whose thickness, composition or both thickness and composition reduce the breakdown voltage exhibited by the heat sink.

10. The device of claim 1, wherein portions of the electrode contact the light emitting element and extend through the heat sink and are coated with insulating material layer that reduces the breakdown voltage exhibited by heat sink.

11. The device of claim 1, wherein the insulating, shielding or other isolating element comprises an insulation material selected from acrylics, acrylates, acrylonitrile-butadiene-styrene (ABS) copolymers, cyanoacrylate adhesives, epoxies, fluorinated ethylene propylene (FEP) elastomers, polycarbonates, polyimides, polytetrafluoroethylene (PTFE) plastics, natural and synthetic rubbers, non-conductive adhesives, RTV and other silicone rubbers, polyurethanes, inorganic dielectrics, glass, ceramics or porcelain.

12. The device of claim 1, wherein the insulating, shielding or other isolating element has a thickness of at least about 0.2 mm.

13. The device of claim 1, wherein the insulating, shielding or other isolating element has a thickness of at least about 0.4 mm.

14. The device of claim 1, wherein the device does not release RF energy from a site other than the electrode tip.

15. An electrosurgical device comprising:
  a) a handle;
  b) a conductive electrode supported by the handle and having a tip for cutting or cauterizing tissue;
  c) an illumination element coupled to the handle, the illumination element comprising a light source, an optical waveguide, and a light emitting element illuminating the electrode tip;
  d) a metallic tubular heat sink surrounding at least part of the conductive electrode and illumination element and having a distal outer edge that abuts against the light emitting element; and
  e) an insulating, shielding or other isolating element that prevents or discourages unintended current flow or plasma formation between the distal outer edge and nearby patient tissue
  wherein the heat sink has inner and outer sidewalls; the insulating, shielding or other isolating element covers at least a portion of the inner sidewall; and the light emitting element has a larger outside diameter than the heat sink and includes a rim portion that extends proximally along at least a portion of the heat sink, and the distal outer edge is buried within and insulated by the rim portion.

16. An electrosurgical device comprising:
  a) a handle;
  b) a conductive electrode supported by the handle and having a tip for cutting or cauterizing tissue;
  c) an illumination element coupled to the handle, the illumination element comprising a light source, an optical waveguide, and a light emitting element illuminating the electrode tip;
  d) a metallic tubular heat sink surrounding at least part of the conductive electrode and illumination element and having a distal outer edge that abuts against the light emitting element; and
  e) an insulating, shielding or other isolating element that prevents or discourages unintended current flow or plasma formation between the distal outer edge and nearby patient tissue
  wherein the heat sink has inner and outer sidewalls; the insulating, shielding or other isolating element covers at least a portion of the inner sidewall; the insulating, shielding or other isolating element also comprises cladding that surrounds the optical waveguide and whose thickness, composition or both thickness and composition reduce the breakdown voltage exhibited by the heat sink; and the device comprises a continuous or discontinuous conductive layer between the cladding and heat shield and connected to an earth ground.

17. An electrosurgical device comprising:
  a) a handle;
  b) a conductive electrode supported by the handle and having a tip for cutting or cauterizing tissue;

c) an illumination element coupled to the handle, the illumination element comprising a light source, an optical waveguide, and a light emitting element illuminating the electrode tip;

d) a metallic tubular heat sink surrounding at least part of the conductive electrode and illumination element and having a distal outer edge that abuts against the light emitting element; and e) an insulating, shielding or other isolating element that prevents or discourages unintended current flow or plasma formation between the distal outer edge and nearby patient tissue wherein the heat sink has inner and outer sidewalls; the insulating, shielding or other isolating element covers at least a portion of the inner sidewall; and all or at least a distal portion of the heat sink is made from an insulating material rather than from metal.

18. An electrosurgical device comprising:
a) a handle;
b) a conductive electrode supported by the handle and having a tip for cutting or cauterizing tissue;
c) an illumination element coupled to the handle, the illumination element comprising a light source, an optical waveguide, and a light emitting element illuminating the electrode tip;
d) a metallic tubular heat sink surrounding at least part of the conductive electrode and illumination element and having a distal outer edge that abuts against the light emitting element; and
e) an insulating, shielding or other isolating element that prevents or discourages unintended current flow or plasma formation between the distal outer edge and nearby patient tissue wherein the heat sink has inner and outer sidewalls; the insulating, shielding or other isolating element covers at least a portion of the inner sidewall; and the insulating, shielding or other isolating element prevents unintended current flow or plasma generation when using an operating power of 10 watts while contacting chicken tissue with the light emitting element, or while laying the heat sink atop such tissue.

19. The device of claim 18, wherein the insulating, shielding or other isolating element prevents unintended current flow or plasma generation when using an operating power of 30 watts while contacting chicken tissue with the light emitting element, or while laying the heat sink atop such tissue.

20. The device of claim 18, wherein the insulating, shielding or other isolating element prevents unintended current flow or plasma generation when using an operating power of 50 watts while contacting chicken tissue with the light emitting element, or while laying the heat sink atop such tissue.

21. The device of claim 18, wherein the insulating, shielding or other isolating element increases the breakdown voltage of the heat sink, measured without the handle and tip, to at least 2 KV RMS @ 20 seconds.

22. The device of claim 18, wherein the insulating, shielding or other isolating element increases the breakdown voltage of the heat sink, measured without the handle and tip, to at least 3 KV RMS @ 20 seconds.

23. The device of claim 18, wherein the insulating, shielding or other isolating element increases the breakdown voltage of the heat sink, measured without the handle and tip, to at least 4 KV RMS @ 20 seconds.

\* \* \* \* \*